(12) United States Patent
Watanabe et al.

(10) Patent No.: US 8,891,089 B2
(45) Date of Patent: Nov. 18, 2014

(54) PHASE OBJECT IDENTIFICATION DEVICE AND METHOD

(75) Inventors: Eriko Watanabe, Kawaguchi (JP); Kashiko Kodate, Tokyo (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 261 days.

(21) Appl. No.: 12/922,542

(22) PCT Filed: Feb. 27, 2009

(86) PCT No.: PCT/JP2009/000879
§ 371 (c)(1),
(2), (4) Date: Nov. 1, 2010

(87) PCT Pub. No.: WO2009/119005
PCT Pub. Date: Oct. 1, 2009

(65) Prior Publication Data
US 2011/0043816 A1    Feb. 24, 2011

(30) Foreign Application Priority Data

Mar. 28, 2008  (JP) .................. 2008-080976

(51) Int. Cl.
  *G01B 9/021*    (2006.01)
  *G01N 21/45*    (2006.01)
  (Continued)

(52) U.S. Cl.
  CPC ........... *G03H 1/0005* (2013.01); *G01N 21/453* (2013.01); *G03H 2001/0072* (2013.01);
  (Continued)

(58) Field of Classification Search
  CPC ......... G01N 21/453; G01J 9/02; G01B 9/021; G01B 9/02047
  USPC ......... 356/512, 515, 521, 605, 618, 457–458, 356/517, 503–504; 359/1, 2, 15, 29, 30, 31
  See application file for complete search history.

(56) References Cited

U.S. PATENT DOCUMENTS 2,950,648 A * 8/1960 Rhodes, Jr. .................. 359/370
3,483,513 A * 12/1969 Burckhardt et al. .......... 382/210
(Continued)

FOREIGN PATENT DOCUMENTS

EP    2264436    12/2010
JP    10-089919    4/1989
(Continued)

OTHER PUBLICATIONS

Ryle et al. (Digital in-lin holography of biological specimens); Proc. of SPIE vol. 6311 (2006).*
(Continued)

*Primary Examiner* — Kara E Geisel
*Assistant Examiner* — Rufus Phillips
(74) *Attorney, Agent, or Firm* — William C. Schrot; Jeffrey I. Auerbach; AuerbachSchrot LLC

(57) ABSTRACT

An object of the invention is to provide a phase object identification device and method which can identify a phase object in a completely different manner from conventional methods for observing or measuring a phase object.
A phase object identification device 1 for identifying a phase object for changing the phase of light includes a light source 2, a sample holding means 3 for holding a phase object 31 to be identified, a holographic recording medium 4 on which a hologram 41 formed by interference between reference light 25 and object light 24 that is phase-modulated by a known phase object 32 is recorded, and a light detector 5, a phase of light 21 emitted from the light source is modulated by the phase object to be identified to generate sample light 22, the hologram of the holographic recording medium is irradiated with the sample light, reproduced light 23 reproduced from the hologram of the holographic recording medium is detected by the light detector.

9 Claims, 9 Drawing Sheets

(51) Int. Cl.
*G01J 9/02* (2006.01)
*G03H 1/00* (2006.01)
*G03H 1/22* (2006.01)
*G03H 1/04* (2006.01)

(52) U.S. Cl.
CPC ........ *G03H 2223/55* (2013.01); *G03H 2210/11* (2013.01); *G03H 1/2286* (2013.01); *G03H 2001/0038* (2013.01); *G03H 2001/0066* (2013.01); *G03H 2223/13* (2013.01); *G03H 2223/12* (2013.01); *G01J 9/02* (2013.01); *G03H 2001/0428* (2013.01); *G03H 2210/12* (2013.01); *G03H 1/041* (2013.01); *G03H 2001/0413* (2013.01); *G03H 2001/2244* (2013.01)
USPC ...................................................... 356/457

(56) References Cited

U.S. PATENT DOCUMENTS 3,624,605 A * 11/1971 Aagard ............ 382/212
4,758,089 A * 7/1988 Yokokura et al. ............ 356/458

FOREIGN PATENT DOCUMENTS

| | | |
|---|---|---|
| JP | 1-300382 | 12/1989 |
| JP | 6-303887 | 11/1994 |
| JP | 2000-113187 | 4/2000 |
| JP | 2006-329722 | 12/2006 |
| WO | WO 2007/073345 | 6/2007 |

OTHER PUBLICATIONS

Charriere et al. ("Cell refractive index tomography by digital holographic microscopy"); Optical Letters vol. 31 No. 2; Jan. 15, 2006.*
Charriere et al. ("Use of digital holographic microscopy in tomography"); Proc. of SPIE 6191, Biophotonics and New Therapy Frontiers, 619100 (Apr. 14, 2006).*
Hanesaka, M. et al. (2007) "2-D Phase Measurement System for Microscopic Objects using Phase Locking Technique", Optics & Photonics Japan 2007, Nov. 26, 2007, p. 272-273.
Watanabe, E. et al. (2006) "Optical Correlator for Face Recognition Using Collinear Holographic System," Japanese Journal of Applied Physics, 45(8B):6759.
Extended European search report of EP09724420.6; 6 pages.
International Preliminary Report on Patentability (WIPO Translation), PCT/JP2009/000879; 5 pages.
International Preliminary Examination Report (WIPO Translation), PCT/JP2009/000879; 5 pages.
International Search Report, PCT/JP2009/000879; 4 pages.

* cited by examiner (A)   (B)

(A)

(B)

(C)

PHASE OBJECT IDENTIFICATION DEVICE AND METHOD

TECHNICAL FIELD

The present invention relates to a phase object identification device and a method for identifying an object (hereinafter, referred to as a "phase object") for changing the phase of light, more particularly, relates to a phase object identification device and a method for identifying a phase object to be identified with the use of holography, and also relates to novel applications using the phase object identification device and the method.

BACKGROUND ART

While the simplest approach for observing an object is an observation by the naked eye, the naked eye is intended to detect the change in light intensity, and thus not suitable for the observation of an object which brings about no change in light intensity or an object which brings about a small change in light intensity. The same applies to common photographs and image sensors because the change in light intensity is detected for the photographs and image sensors. For example, biological cells, bacteria, gratings, waveguides, microscopic steps at the surfaces of objects, structure of the same color, etc. bring about no changes or only small changes in light intensity, and it has been thus difficult to observe the shapes thereof. In particular, biological cells have many clear and colorless intercellular components, and it has been thus extremely difficult to observe the shape and intercellular components of the biological cells.

Therefore, conventionally, biological cells are subjected to a pretreatment for dyeing the biological cells to visualize the shapes thereof or identify of each intercellular component depending on the degree of dyeing. While biological cells can be visualized by dyeing, the dyeing technique is not able to be used in some cases depending on targets. In addition, the pretreatment for dyeing requires time for immobilization, etc of biological cells, which is not a simple approach for observation. Furthermore, the dyeing may cause the biological cells to die or alter the biological cells, thereby resulting in the problems of failure to observe the biological cells under normal conditions and limitation to subsequent uses of the samples.

In the meanwhile, objects which bring about no changes in light intensity even change the phase of light in response to the difference in refractive index or the optical path difference in many cases. The biological cells, bacteria, gratings, waveguides, microscopic steps at the surfaces of objects, structure of the same color, etc. mentioned above are also included in phase objects which modulate the shape of light. In the case of such phase objects, it is possible to observe the phase objects by a phase-contrast microscope, a differential interference microscope, or the like converting relative phase information into intensity. In addition, as described in Non-Patent Document 1, techniques for measuring absolute phase information on phase objects have been also researched and developed. In Non-Patent Document 1, the closed-loop feedback technique is introduced into a Mach-Zehnder interferometer, and the entire surfaces of phase objects are scanned by the phase measurement system which is capable of measuring changes in phase in microscopic regions of clear and colorless phase objects with a high degree of accuracy, thereby measuring absolute phase information on the clear and colorless phase objects.

Non-Patent Document 1: Mai HANESAKA, Eriko WATANABE, Jun MIZUNO, and Kashiko KODATE, "2-D Phase Measurement System for Microscopic Objects using Phase Locking Technique", Optics & Photonics Japan 2007, Nov. 26, 2007, p.272-273

DISCLOSURE OF THE INVENTION

Problems To Be Solved By the Invention

In recent years, the discovery of an embryonic stem cell (ES cell) has expanded the possibilities of further regenerative medical techniques, and various types of research and development have been actively carried out. The ES cells refer to pluripotent stem cells established from early embryos of animals, and cells which potentially differentiate into all cells. Moreover, the ES cells can be cultured and proliferated while keeping the pluripotent differentiation, and intended cells, organs, and tissues have been thus expected to be created and used for treatments. While cell transplantation using living cells, such as skin transplantation, bone-marrow transplantation, and organ transplantation, has major problems such as a scarcity of donors and rejections, the discovery of the ES cells has been showing some signs of solving the problems.

In addition, cytoscreening has been frequently carried out in which cells collected from a lesion and cultured are observed under a microscope to detect abnormal cells, tumor cells, and the like, thereby making a diagnosis of the presence or absence of a lesion or a diagnosis of a lesion, because the cytoscreening is relatively easy to carry out and lessens the burden on patients.

In these cell culture techniques, the presence or absence of a nucleus has importance. More specifically, if there is no nucleus inside a cell, no cell division will be caused, resulting in failure to create any cells. Therefore, it has been necessary to examine the presence or absence of a nucleus inside a cell. As described above, the observation of dyed cells is unfit for the examination, because the observation takes time and cause biological cells to die or alter the biological cells. In addition, while living cells can be observed in the observation by a phase-contrast microscope, a differential interference microscope, or the like, which is an examination carried out by the naked eye, the accuracy of the examination is greatly affected by the skill and experience of the observer. The case of the measurement with the use of the phase measurement system has the problem of investment of time for the measurement.

An object of the invention is to provide a phase object identification device and method which can identify a phase object in a completely different manner from conventional methods for observing or measuring a phase object. In addition, another object of the present invention is to provide novel applications using the phase object identification device and method. An object of the present invention is to provide an examination device and an examination method for the nucleus of the biological cell described above as one of the applications.

Means For Solving the Problems

In order to solve the problems, a phase object identification device for identifying a phase object for changing the phase of light according to the present invention is characterized in that it comprises: a light source; a sample holding means for holding a phase object to be identified; a holographic recording medium on which a hologram formed by interference between reference light and object light that is phase-modulated by a known phase object is recorded; and a light detector, a phase of light emitted from the light source is modulated by the phase object to be identified to generate sample light, the hologram of the holographic recording medium is irradiated with the sample light, reproduced light reproduced from the hologram of the holographic recording medium is detected by the light detector.

In the phase object identification device, it is preferable that the hologram of the holographic recording medium be irradiated with the sample light by an objective lens arranged in such a way that a real image of the phase object to be identified is located on an incident pupil plane.

In the phase object identification device, it is preferable that multiple holograms formed from multiple known phase objects are recorded on the holographic recording medium, and the phase object identification device comprises an irradiated position shifting means for shifting a position irradiated with the sample light in the holographic recording medium.

In addition, it is preferable that the phase object identification device comprise an observation optical system for observing a phase object to be identified, which is held by the sample holding means, and the observation optical system comprise a sample-side objective lens, and an imaging lens or an eyepiece. Furthermore, it is preferable that the sample holding means comprise a focusing means for shifting a phase object to be identified in an optical axis direction or a sample positioning means for shifting a phase object to be identified in a planar direction orthogonal to the optical axis, in order to observe a held phase object to be identified by the observation optical system.

In addition, the phase object identification device may comprise a sample conveying means for sequentially conveying multiple phase objects to be identified to the sample holding means.

In addition, in the phase object identification device, the phase object to be identified may be a biological cell or a bacterium, and the presence or absence of a cell nucleus in the biological cell or the bacterium may be identified. Alternatively, the known phase object may be a specimen within standards, and whether or not the phase object to be identified corresponds to the standards may be identified.

In addition, it is preferable that the phase object identification device comprise a reference light generation means for generating reference light, the sample holding means be able to hold a known phase object, a phase of light emitted from the light source be modulated by the known phase object to generate object light, the reference light generation means generate reference light, the holographic recording medium be irradiated with the object light and the reference light, and a hologram formed by interference between the object light and the reference light be recorded on the holographic recording medium. Furthermore, the reference light generation means may be an opening formed in the sample holding means.

A phase object identification method according to the present invention is a phase object identification method for identifying a phase object for changing the phase of light, characterized in that: a phase of light emitted from a light source is modulated by a phase object to be identified to generate sample light; a holographic recording medium, on which a hologram formed by interference between reference light and object light that is phase-modulated by a known phase object is recorded, is irradiated with the sample light; reproduced light reproduced from the hologram of the holographic recording medium is detected by a light detector; and the phase object to be identified is identified as having a correlation with the known phase object if the intensity of the reproduced light detected by the light detector is greater than a threshold value, or the phase object to be identified is identified as having no correlation with the known phase object if the intensity of the reproduced light is less than the threshold value.

Advantageous Effects of the Invention

The phase object identification device and method according to the present invention are essentially different in technical idea from the prior art in which the phase modulation pattern itself of a phase object to be identified is identified by converting the change in phase of light caused by the phase object into the change in light intensity, and provided to detect the correlation between a phase to be identified and a known phase object for identifying the phase object to be identified. Furthermore, the phase object identification device and method according to the present invention also have a big feature in that the correlation between a phase to be identified and a known phase object is detected by the calculation of optical correlation with the use of holography.

The holography refers to a technique which is capable of recording the amplitude (intensity) and phase of light, which is able to record phase information on a known phase object directly as a hologram. More specifically, when a recording medium is irradiated with object light that is phase-modulated by a known phase object and reference light so as to overlap the object light and the reference light with each other in a hologram recording layer of the recording medium, the hologram formed by interference between the object light and the reference light can cause a photoreaction of a photosensitive material in the hologram recording layer and set the hologram in the hologram recording layer.

When the thus recorded hologram on the recording medium is irradiated with the object light that is phase-modulated by the known phase object under the same conditions as in the case of recording, the object light is diffracted by the hologram to generate reproduced light corresponding to the reference light. Furthermore, even when the hologram is irradiated with light that is phase-modulated by a phase object which has a correlation with the known phase object, rather than by the known phase object, under the same conditions as in the case of recording, the hologram will characteristically interfere with the light to generate reproduced light depending on the correlation value (the degree of similarity). Therefore, the detection of the presence or absence of reproduced light can identify the presence or absence of correlation between the phase object to be identified and the known phase object. More specifically, unless any reproduced light is reproduced from the hologram irradiated with the sample light under the same conditions as in the case of recording to generate any reproduced light from the hologram, the phase object to be identified can be identified as having no correlation with the known phase object, or if reproduced light is generated, the phase object to be identified can be identified as having a correlation with the known phase object. Furthermore, the detection of the intensity of reproduced light also allows the degree of correlation to be identified. Other advantageous effects of the phase object identification device and method for identifying a phase object according to the present invention will be described in the following embodiments.

BEST MODE FOR CARRYING OUT THE INVENTION

Figure 1:
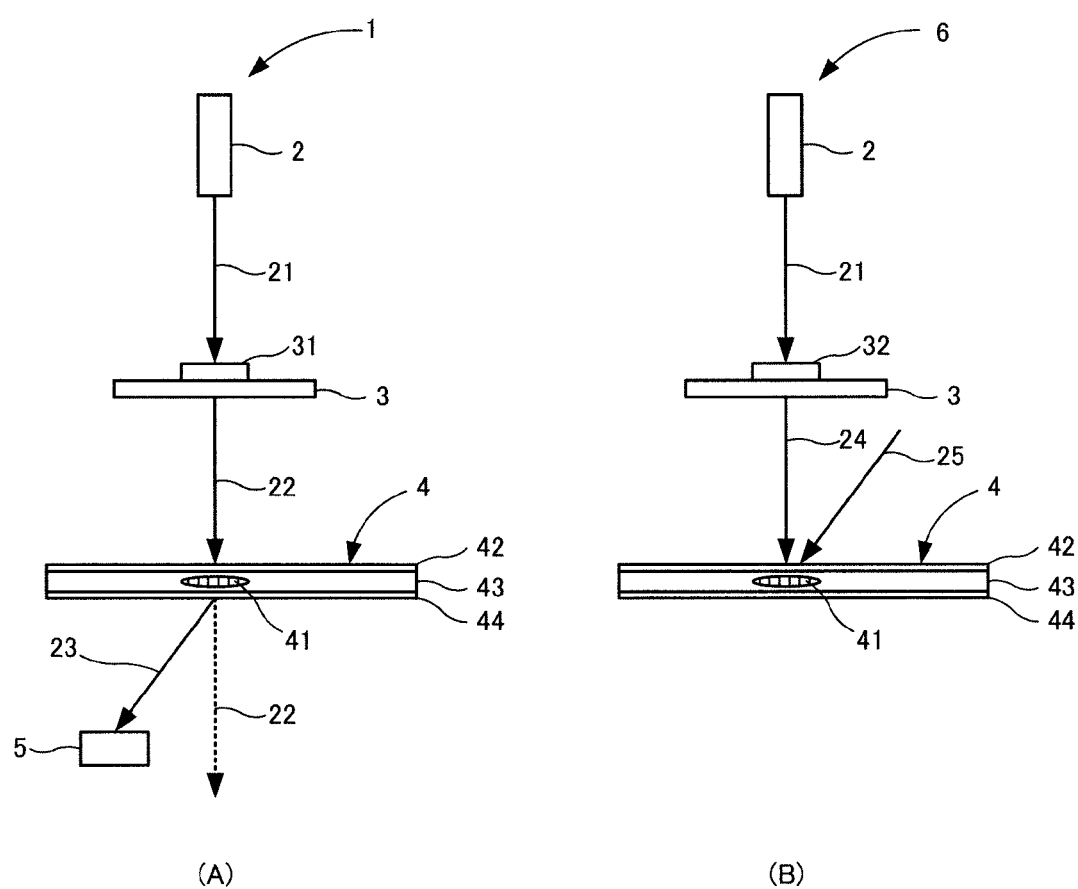
[FIG. 1] (A) a pattern diagram for explaining the basic principle for a phase object identification device and method according to the present invention; and (B) a pattern diagram for explaining the basic principle for a recording device and a method.

While embodiments of the present invention will be described below with reference to the drawings, the present invention is not to be considered limited to the following examples. FIG. 1(A) is a pattern diagram for explaining the basic principle for a phase object identification device and method according to the present invention. In FIG. 1(A), a phase object identification device 1 includes a light source 2, a sample holding means 3 in which a phase object 31 (hereinafter, also referred to as a sample) to be identified is held, a holographic recording medium 4 on which a hologram 41 is recorded, and a light detector 5. Further, FIG. 1(B) is a pattern diagram for explaining the basic principle for a recording device 6 and a method for recording the hologram 41 on the holographic recording medium 4 in the phase object identification device 1. It is to be noted that various types of lenses in the specification include both single lenses and lens groups of multiple lenses combined.

The light source 2 emits coherent light in phase, and it is preferable to use a laser light source as the light source 2. Light 21 emitted from the light source 2 is processed by an optical system, not shown, into a plane wave which has a larger cross section than the sample 31.

The sample holding means 3 is provided to place the sample 31 in the phase object identification device 1, and as the sample holding means 3, various types of holding means can be selected depending on the sample 31. For example, the sample 31 may be simply placed on the sample holding means 3, or may be fixed to the sample holding means 3 with vacuum adsorption, a fixation device, or the like. In order to reduce the attachment of dirt and dust, the fixed sample 31 is preferably arranged in a vertical direction, or placed on the undersurface of the sample holding means 3. In addition, the sample 31 may be secured with a clip or the like, or in the case of the sample 31 in the form of a thin piece, a structure can be adopted in which the sample 31 is inserted into a slit provided in the holding means. While the sample 31 may be directly held in the sample holding means 3, the sample 31 in an aid such as a container or a mounting device may be held in the sample holding means 3. For example, a microplate or preparation with the sample 31 therein may be held in the sample holding means 3.

The phase object 31 to be identified may be any phase object which at least changes the phase of light, which may or may not change the intensity of light. For example, biological cells, bacteria, gratings, waveguides, microscopic steps at the surfaces of objects, structure of the same color, etc. can be used as the phase object 31 to be identified. In addition, the phase object 31 to be identified is not to be considered limited to solids, and encompasses, for example, orientation structures of liquid crystals, and the like.

The sample holding means 3 and the sample 31 held therein serve as a sample light production means for modulating at least the phase of the light 21 emitted from the light source 2 to produce sample light 22. While the sample 31 is a phase object for modulating at least the phase of light, the phase object may further modulate the intensity of light. As shown in FIG. 1(A), in the case of a transmission-type sample light production means which transmits the light 21 from the light source through the sample 31 and the sample holding means 3 to produce the sample light 22, at least a region of the sample holding means 3 in which the sample 31 is located needs to be configured so as not to block light. For example, a transparent material may be used for the region of the sample holding means 3 in which the sample 31 is located, or the sample 31 placed in a transparent container or mounting device may be held by the sample holding means 3 with an opening in the region of the sample holding means 3 in which the sample 31 is located. The sample holding means 3 in such a transmission-type sample light production means can be used as a mask for producing object light 24 and reference light 25 in the recording device 6 described later. It is to be noted that in the case of preparing a reflection-type sample light production means, the surface of the sample holding means 3 is made with a mirror surface in such a way that light transmitting through the sample 31 is reflected to produce sample light 22. The case of a reflection-type sample light production means requires an optical system such as a beam splitter for separating the light 21 from the light source for irradiating the sample holding means 3 and the sample light 22.

On the holographic recording medium 4, the hologram 41 is recorded which is formed by interference between reference light 25 and objet light 24 that is phase-modulated by a known phase object (see FIG. 1(B) for the object light 24 and the reference light 25). The holographic recording medium 4 may be a transmission-type or reflection-type holographic recording medium, and FIG. 1(A) shows a transmission-type holographic recording medium. The holographic recording medium 4 in FIG. 1(A) has a structure of a hologram recording layer 43 interposed between a pair of light-transmitting substrates 42 and 44. In the case of preparing a reflection-type holographic recording medium, a reflective layer may be provided on the rear side from the hologram recording layer 43 while the light incidence side of the holographic recording medium is used as a front surface. For example, when a reflective layer is provided on the front surface or rear surface of the substrate 44, a reflection-type holographic recording medium can be prepared.

The known phase object refers to a phase object which has at least some information or characteristics identified. For example, known phase objects include phase objects and phase patterns with their phase modulation patterns identified, biological cells and bacteria with their names identified, biological cells and bacteria with their active reactions identified, phase patterns of cell nuclei, specimens of phase objects (products with microscopic steps and structures of the same color) within standards (within dimension tolerances), and gratings with their intervals identified.

When the hologram 41 of the holographic recording medium 4 is irradiated with the sample light 22, reproduced light 23 is reproduced depending on the degree of interference between the sample light 22 and hologram 41. The reproduced light 23 refers to light corresponding to the reference light 25 emitted when the hologram 41 is recorded. The cross-sectional shape and travelling direction of the reference light 25 is reflected on the cross-sectional shape and travelling direction of the reproduced light 23. The degree of interference corresponds to a correlation value (the degree of similarity) between the known phase object with the object light for recording the hologram 41 and the sample 31 which is a phase object to be identified. Therefore, when the sample 31 is the same as the known phase object, the correlation value is the maximum because of autocorrelation, and intense reproduced light is reproduced. When the sample 31 is different from but similar to the known phase object, reproduced light is reproduced which has an intensity depending on the degree of similarity. Furthermore, when the sample 31 is completely different from the known phase object, reproduced light is not reproduced. It is to be noted that the sample light 22 transmitting through the holographic recording medium 4 (indicated by a dotted line in FIG. 1(A)) is blocked or separated from the reproduced light 23 by a mask not shown or an optical system for separation so as not to reach the light detector 5.

The light detector 5 is provided to detect the reproduced light 23 reproduced from the hologram 41 of the holographic recording medium 4, which can preferably detects the light intensity. As the light detector 5, highly sensitive light detection elements such as photomultiplier tubes (PMT) and avalanche photo diodes, and inexpensive small-sized semiconductor detectors, for example, PIN photodiodes, CMOS sensors, and CCD sensors, etc. can be used. When the cross-sectional shape of the reproduced light 23 is smaller than the light receiving region of the light detector 5, the light detector including one light detection element can directly be used. On the other hand, when the cross-sectional shape of the reproduced light 23 is larger than the light receiving region of the light detector 5, the light detector including one light detection element can be used by light collection through a collecting lens. In addition, the light detector 5 including multiple light detection elements can be used, and in such a case, the light intensity of the reproduced light can also be detected by obtaining the sum of the intensities from all of the light detection elements. Even when the cross-sectional shape of the reproduced light 23 is smaller than the light receiving region of the light detector 5, the use of a collecting lens can improve the reliability. It is to be noted that the cross-sectional shape of the reproduced light 23 is determined by the cross-sectional shape of the reference light for recording.

As described above, the detection of the presence or absence of the reproduced light 23 can identify whether or not the phase object 31 to be identified is correlated with the known phase object. More specifically, unless any reproduced light is reproduced from the hologram irradiated with the sample light under the same condition as in the case of recording, the phase object to be identified can be identified as having no correlation with the known phase object. If reproduced light is generated, the phase object to be identified can be identified as having a correlation with the known phase object. Furthermore, the detection of the intensity of the reproduced light also allows the degree of correlation to be identified.

For example, even in the case of only identifying the presence or absence of any correlation, the use of a known biological cell or bacterium with a cell nucleus as the known phase object and the use of a collected and cultured biological cell or bacterium as the phase object to be identified makes it possible to utilize the identification of the presence or absence of correlation for an examination for identifying whether or not the collected and cultured biological cell or bacterium has a cell nucleus. In addition, the identification with the use of a specimen within standards as the known phase object and with the use of a produced product as the phase object to be identified makes it possible to identify whether or not the produced product corresponds to the standards. For example, the identification can be utilized for examinations on errors in diffraction grating period of grating elements and on the three-dimensional shapes of structures of the same color. In these examinations, the sample holding means 3 is preferably provided with a sample conveying means for sequentially conveying the samples 31 to the sample holding means 3 in order to examine a large number of samples continuously.

In addition, multiple holograms 41 are irradiated with the sample light 22 to identify the presence or absence of correlation with multiple known phase objects, thereby allowing the sample 31 to be specified. In order to irradiate the multiple holograms 41 with the sample light 22, it is more preferable to record, on the holographic recording medium 4, multiple holograms 41 formed with the use of multiple known phase objects and provide a irradiated position shifting means for shifting the position irradiated with the sample light 22 in the holographic recording medium 4, while the holographic recording medium 4 itself may be replaced with another holographic recording medium 4 on which a hologram 41 is recorded and irradiated with the sample light 22.

While the irradiated position shifting means includes a system of shifting the sample light 22, a system of shifting the holographic recording medium 4, and a system of shifting both the sample light 22 and the holographic recording medium 4, the system of fixing the sample light 22 and shifting the holographic recording medium 4 is preferable in order to prevent the position of the optical system from getting out of alignment due to vibrations, etc. associated with shifting. For example, the holographic recording medium 4 may be shifted with the use of a XY stage in planar directions orthogonal to the optical axis, or the holographic recording medium 4 may be rotated with the use of a motor.

The recording device 6 in FIG. 1(B) is intended to produce the holographic recording medium 4 for use in the phase object identification device 1, which irradiates the holographic recording medium 4 with the object light 24 and the reference light 25 and records, on the holographic recording medium 4, the hologram 41 formed by interference between the object light 24 and the reference light 25. The hologram 41 herein recorded on the holographic recording medium 4 in the recording device 6 has to interfere with the sample light 22 to generate the reproduced light 23 in the phase object identification device 1. For this purpose, it is necessary to irradiate the holographic recording medium 4 with the object light 24 which has the same wavelength as the sample light 22 under the same irradiation conditions (incidence angle, magnification ratio, focal point). As the simplest approach, the configuration of the phase object identification device 1 for generating the sample light 22 and irradiating the holographic recording medium 4 with the sample light 22 may be conformed to the configuration of the recording device 6 for generating the object light 24 and irradiating the holographic recording medium 4 with the object light 24. This approach means that a device can be produced which has the both functions of the phase object identification device 1 and the recording device 6. However, the light detector 5 for detecting reproduced light is separately required for the phase object identification device 1, whereas a reference light generation means for generating reference light is separately required for the recording device 6. In this specification, the descriptions of the respective configurations of the phase object identification device 1 or the recording device 6 are basically incorporated in the description of the common configuration of the other device.

The recording device 6 in FIG. 1(B) uses the same configuration (denoted by the same reference numerals) as the configuration in FIG. 1(A) for generating the sample light 22 and irradiating the holographic recording medium 4 with the sample light 22 in the same arrangement. More specifically, the recording device 6 in FIG. 1(B) includes the light source 2, the sample holding means 3, and the holographic recording medium 4. However, in the recording device 6, the sample holding means 3 holds a known phase object 32, and the sample holding means 3 and the known phase object 32 serve as an object light generation means for generating the object light 24 with the use of light 21 from the light source 2. In addition, the holographic recording medium 4 is irradiated with the reference light 25 generated by a reference light generation means, not shown. The hologram formed by interference between the object light 24 and the reference light 25 can cause a photoreaction of a photosensitive material in the hologram recording layer 43 and set the hologram 41 in the hologram recording layer 43.

In the case of recording multiple holograms 41 on the holographic recording medium 4, the irradiated position shifting means may be used to shift the positions irradiated with the object light 24 and the reference light 25 in the holographic recording medium and irradiate other positions with object light 24 formed by another known phase object 32 and reference light 25 to record another hologram 41.

As the object light generation means, a phase spatial light modulator can also be used, besides the method of using the known phase object 32. As the phase spatial light modulator, for example, a phase-modulation type liquid crystal display device can be adopted, on which a phase pattern of a known phase object may be displayed. In the case of using the phase spatial light modulator, simply changing the display on the phase spatial light modulator can preferably generate another object light when multiple holograms 41 are to be recorded.

While the reference light generation means preferably generates the reference light 25 with the use of light 11 from the light source 1, light from other light source may be used which interferes with the object light 24. The holographic recording medium 4 is irradiated with the reference light 25 so as to intersect with the object light 24. For the reference light, divergent light in a smaller region as compared with the object light and a bundle of spatially separated multiple rays can be used. While a two-beam interference type optical system can also be used in which the optical axis of the object light 24 is different from the axis of the reference light 25, it is preferable to record the hologram 41 with the use of a collinear optical system. The collinear optical system will be described in detail with reference to FIG. 2.

While the present invention has been described with reference to the minimum required configurations in FIGS. 1(A) and 1(B) in order to explain the basic principle, the present invention is not to be considered limited to devices which have only the configurations, and even more configurations can be added in response to desired effects. For example, it is preferable to record a Fourier image of the known phase object 32 as the hologram 41, rather than recording a real image of the known phase object 32. For this purpose, an objective lens arranged so that real images of the sample light 22 and the object light 24 are located on the incident pupil plane may be adopted in such a way that the objective lens is used to irradiate the holographic recording mediums with the sample light 22 and the object light 24. The Fourier image is not the shape of a phase pattern, but the spatial frequency distribution of a phase pattern, and thus allows tendency correlation of a pattern to be identified, rather than simple shape correlation.

In addition, it is also preferable to include an observation optical system for observing the sample 31 and the known phase object 32. Furthermore, in order to identify multiple samples continuously, the sample holding means 3 preferably includes a sample conveying means for sequentially conveying the multiple samples 31.

Figure 2:
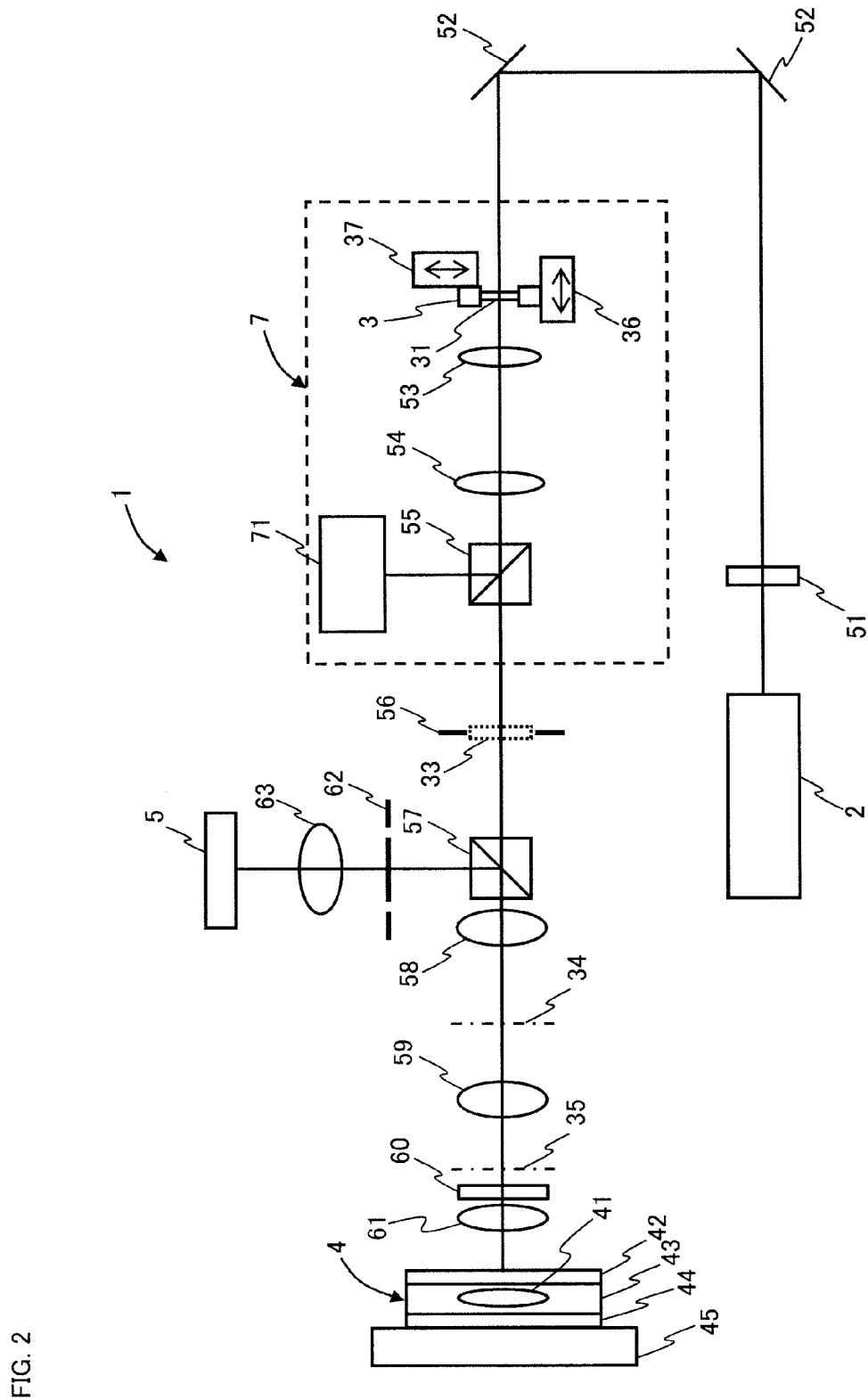
[FIG. 2] a configuration diagram schematically illustrating an embodiment of a phase object identification device according to the present invention which is also available as a recording device.

FIG. 2 is a configuration diagram schematically illustrating an embodiment of a phase object identification device 1 which is also available as a recording device 6 for recording a hologram 41 with the use of a collinear optical system. The phase object identification device 1 in FIG. 2 further includes an observation optical system 7 and an image sensor 71 for observation for observing a sample or a known phase object (hereinafter, the sample and the known phase object are collectively referred to as "a sample and the like"). It is to be noted that a reflection-type holographic recording medium 4 is used in the phase object identification device 1 in FIG. 2.

The phase object identification device 1 includes an optical system for generating sample light, irradiating the holographic recording medium 4 with the sample light, and detecting reproduced light, in addition to a light source 2, a sample holding means 3, a holographic recording medium 4, and a light detector 5, and the optical system also includes the observation optical system 7 for observing a sample and the like. The optical system includes a beam shaping optical system 51, a pair of mirrors 52, a sample-side objective lens 53, an imaging lens 54, a beam splitter 55, a mask 56, a polarization beam splitter 57, a first relay lens 58, a second relay lens 59, a quarter wavelength plate 60, an objective lens 61, an aperture 62, and a collecting lens 63.

The light source 2 serves as a light source for object light and reference light for recording a hologram, and also serves as a light source for sample light for identifying a sample 31. Furthermore, in FIG. 2, the sample light 2 is also used as a light source for observing a sample and the like in the observation optical system 7. However, it is preferable to separately prepare a light source which is suitable for observation, rather than the light source 2, as the light source for the observation optical system. As the light source 2, for example, a YVO4 laser of 532 nm can be used. It is to be noted that as the light source 2, light is selected which has a wavelength to which a photosensitive material in a hologram recording layer 43 of the holographic recording medium 4 is sensitive.

The beam shaping optical system 51 is provided, if necessary, for converting the shape of light emitted from the light source 2, and for example, includes a collimator lens for processing divergent light into parallel light, and a beam expander for increasing the apertures of beams.

The pair of mirrors 52 is provided to direct the travelling direction of light emitted from the light source 2 to a sample and the like. In FIG. 2, the pair of mirrors 52 changes the travelling direction of light emitted from the light source 2 by 180° to reduce the size of the device. The means for directing the travelling direction of light to a sample and the like is not to be considered limited to the configuration of the pair of mirrors 52, and an appropriate configuration is adopted as the means, depending on the configuration of the optical system. For example, prisms, deflection elements, and the like can also be used instead of mirrors, or if the travelling direction of light emitted from the light source 2 is directly directed to a sample and the like, the means for directing the travelling direction of light to a sample and the like is never necessary.

The sample holding means 3 is provided to hold a sample and the like. In FIG. 2, the sample holding means 3 has an opening for a region to be irradiated with light, and the sample 31 is held in the opening region. In the phase object identification device 1 in FIG. 2, the sample and the like held in the sample holding means 3 can be observed by the observation optical system 7 and the image sensor 71 for observation.

The observation optical system 7 is intended to form an image of a sample and the like on a light receiving surface of the image sensor 71 for observation and a plane 33 (the position in which the mask 56 is placed) conjugate to the light receiving surface, and an incident pupil plane 35 of an objective lens, and it is possible for the observation optical system 7 to use optical systems of various types of microscopes. In FIG. 2, the observation optical system 7 includes the sample-side objective lens 53 and the imaging lens 54, which allows a sample and the like to be observed in a bright field. In the case of a small sample and the like, the sample-side objective lens 53 and the imaging lens 54 can preferably enlarge an image of a sample and the like. In addition, for the sample-side objective lens 53, multiple lenses which are different in magnification ratio can be preferably switched in order to make the observation easier. Furthermore, an eyepiece for observation by the naked eye may be provided in combination with the imaging lens 54 or instead of the imaging lens 54.

Furthermore, in the case of including the observation optical system 7 as shown in FIG. 2, the sample holding means 3 preferably includes a focusing means 36 for adjusting the focal points of a sample and the like and/or a sample positioning means 37 for adjusting the positions of a sample and the like. The focusing means 36 is a means for shifting the phase object (sample 31) to be identified and the known phase object 32 in the direction of the optical axis, which is provided to form an image of a sample and the like on imaging planes (the light receiving surface of the image sensor 71, the position 33, and the position 35). The focusing means 36 is used to shift the sample 31 and the like manually or electrically in the direction of the optical axis (Z axis direction). In addition, the sample positioning means 37 is a means for shifting the phase object (sample 31) to be identified and the known phase object 32 in the planar directions orthogonal to the optical axis, which is provided to place the sample 31 and the like in the field for observation. The sample positioning means 37 is used to shift the sample 31 and the like manually or electrically in the planar directions (X axis direction and Y axis direction) orthogonal to the optical axis. Various types of moving mechanism can be used as the focusing means 36 and the sample positioning means 37, and for example, a XYZ driven stage or the like can be used which includes an adjusting mechanism for slight movements.

As the image sensor 71 for observation, CCDs and CMOS sensors can be used. The image sensor 71 for observation is connected to a monitor or a recording medium, not shown, so that images acquired by the image sensor 71 for observation, can be displayed on the monitor or recorded on the recording medium. When the focusing means 36 and the sample positioning means 37 are used to make an adjustment so that an image of a sample and the like is formed on the center of the optical axis while observing the sample and the like by the image sensor 71 for observation, the accuracy of identification can be improved dramatically. In addition, when the observation optical system 7 is used to adjust the magnification ratio for the sample and the like, the size of the phase object to serve as a basis for the object light and the sample light can be standardized. The observation optical system 7 forms, in the position 33, the same image as the image formed on the light receiving surface of the image sensor 71 for observation, and the holographic recording medium 4 is irradiated with the image in the position 33 as sample light and object light. When the image in the position 33 (the image observed by the image sensor 71 for observation) is formed to have the same size, the difference in size between a sample and the like can be corrected.

It is possible to utilize the configurations of conventional optical microscopes for the observation optical system 7, the sample holding means 3, the focusing means 36, the sample positioning means 37, and the image sensor 71 for observation, which are provided to observe the sample 31 and the like. Since the observation in a bright field is difficult when the intensity of light is not modulated by the sample and the like or when the difference in intensity is small, it is preferable to adopt observation in a dark field or a configuration in which the observation is possible even with the use of a phase-contrast microscope or a differential interference microscope.

The beam splitter 55 is an optical element which partially reflects incident light and transmits the other of the incident light, and splits light from a sample and the like to generate light directed to the image sensor 71 for observation and light directed to the holographic recording medium 4. The beam splitter 55, which divides light, may be provided with an optical element for switching the travelling direction of light. For example, a movable mirror can be provided instead of the beam splitter 55, in such a way that light from a sample and the like can be reflected toward the image sensor 71 for observation in the case of observing a sample and the like, and the mirror can also be moved out of the optical axis to direct light from the sample and the like toward the holographic recording medium 4 in the case of identifying the sample and the like.

The mask 56 is arranged on the imaging plane on which an image of the sample and the like is formed by the observation optical system 7 or in the position of the sample holding means. For identification, a mask is arranged for forming the profile of sample light, and for recording, another mask is arranged for forming the profile of object light and producing the intensity pattern of reference light. The mask 56 may be arranged in the position of the sample and the like (that is, the sample holding means 3) or on other imaging plane (the incident pupil plane 35 of the objective lens), rather than in the position 33. For example, the profile of the sample light, the profile of the object light, and the intensity pattern of reference light may be formed with the opening of the sample holding means 3 as the mask 56, or the mask 56 may be arranged on the incident pupil plane 35 of the objective lens. It is to be noted that the generation of the sample light and object light themselves is achieved by being modulated by the sample and the like, whereas the mask 56 is provided to form the profiles of the sample light and object light.

Figure 3:
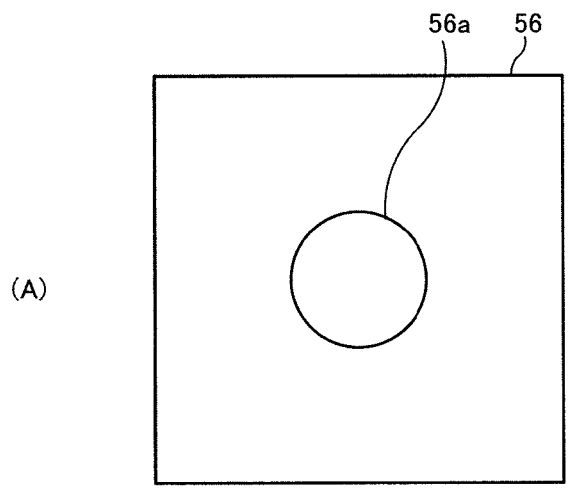
[FIG. 3] (A) a diagram illustrating an example of a mask shape for forming the profile of sample light; (B) a diagram illustrating an example of a mask shape for forming the profile of object light and the intensity pattern of reference light; and (C) a diagram illustrating an example of an aperture shape.
Figure 3:
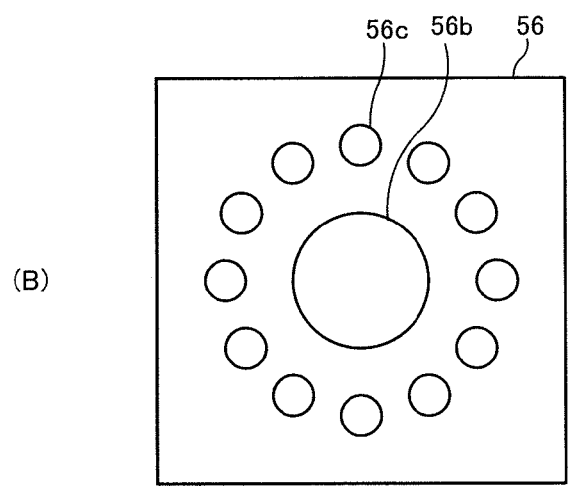
Figure 3:
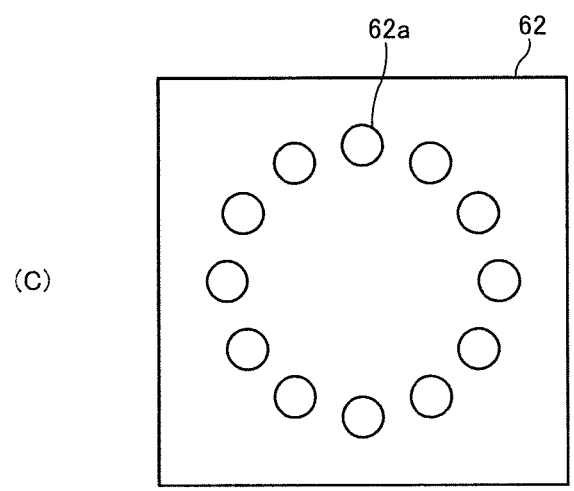

FIG. 3(A) is an example of a mask 56 for forming the profile of sample light in the case of identification, and FIG. 3(B) is an example of a mask 56 for producing the profile of object light and the intensity pattern of reference light in the case of recording. In FIG. 3(A), the mask 56 has a circular opening 56a provided in the center, and light can be transmitted through the mask 56 to form the profile of the sample light into a circular shape. In FIG. 3(B), the mask 56 has a circular opening 56b provided in the center, and twelve small circular openings 56c provided in a radial fashion around the circular opening 56b, and light can be transmitted through the opening 56b and the openings 56c respectively to form the profile of the object light into a circular shape and generate reference light arranged in a pattern composed of twelve small circular shapes arranged in a radial fashion around the object light. The mask 56 is formed from a material which is able to block light from the light source 2. It is to be noted that the mask for recording and the mask for identification may be switched by flip of a switch, or the openings 56c may be provided with a shutter to close the shutter for identification.

The polarization beam splitter 57 is provided to transmit one of mutually orthogonal polarization directions and reflects the other, and provided along with the quarter wavelength plate 60 in order to separate sample light, object light, and reference light toward the holographic recording medium 4 from reproduced light reproduced from the holographic recording medium 4. In FIG. 2, the polarization beam splitter 57 transmits the sample light, object light, and reference light toward the holographic recording medium 4, and reflects the reproduced light reproduced from the holographic recording medium 4 toward the light detector 5. Depending on the configuration of the optical system, the polarization beam splitter 57 may be configured so as to reflect the sample light, object light, and reference light toward the holographic recording medium 4 and transmit the reproduced light toward the light detector 5.

The first relay lens 58 and the second relay lens 59 are an example of an optical system for forming an image of a sample and the like formed in the position 33 onto the incident pupil plane 35 of the objective lens 61. The first relay lens 58 is arranged so that the interval from the position 33 to the first relay lens 58 and the interval from the first relay lens 58 to a Fourier plane 34 correspond to the focal length of the first relay lens 58. In addition, the second relay lens 59 is arranged so that the interval from the Fourier plane 34 to the second relay lens 59 and the interval from the second relay lens 59 to the incident pupil plane 35 correspond to the focal length of the second relay lens 59. The optical system is not to be considered limited to the configuration of the first and second relay lenses 58 and 59, and various imaging optical systems can be used.

The quarter wavelength plate 60 is provided to convert linearly polarized light into circularly polarized light. Light can be transmitted through the quarter wavelength plate 60 twice to rotate linearly polarized light by 90 degrees. Reproduced light reproduced from the hologram 41 by sample light irradiation corresponds to reference light for recording. The reference light has been once transmitted through the quarter wavelength plate 60 when the hologram 41 is to be recorded, thus, the transmission of the reference light through the quarter wavelength plate 60 again results in linearly polarized light in a polarization direction which is orthogonal as compared with the reference light before the transmission through the quarter wavelength plate 60 for recording, and the linearly polarized light can be separated by the polarization beam splitter 57.

The objective lens 61 is provided to apply Fourier transformation to sample light, object light, and reference light and irradiate the holographic recording medium 4 with the sample light, object light, and reference light. In addition, when the reflection-type holographic recording medium 4 is used as shown in FIG. 2, the objective lens 61 forms an image of reproduced light reproduced from the hologram 41 onto an exit pupil plane. In order to apply Fourier transformation to sample light, object light, and reference light, the imaging optical systems 53, 54, 58, and 59 are used to form an image of a sample and the like or the intensity pattern of reference light onto the incident pupil plane 35 of the objective lens 61.

The holographic recording medium 4 in FIG. 2 has a reflection-type structure of a hologram recording layer 43 interposed between a transparent substrate 42 and a substrate 44 with a reflective layer. When the phase object identification device 1 functions as the recording device 6, the holographic recording medium 4 is irradiated with object light and reference light to record the hologram 41 on the hologram recording layer 43. Alternatively, when the phase object identification device 1 identifies a phase object, the holographic recording medium 4 is irradiated with sample light, and the sample light is emitted from the incidence plane side of the holographic recording medium 4, along with reproduced light reproduced from the hologram 41.

The holographic recording medium 4 is held on a recording medium shifting means 45 for shifting the holographic recording medium 4. The recording medium shifting means 45 is able to shift or rotate the holographic recording medium 4 in directions orthogonal to the optical axis, in such a way that the positions irradiated with sample light, object light, and reference light in the holographic recording medium 4 can be shifted to record multiple holograms on the holographic recording medium 4 and optical correlation can be calculated between the multiple holograms 41 on the holographic recording medium 4 and sample light.

The aperture 62 has an opening which blocks sample light reflected by the reflection-type holographic recording medium 4 and transmits only reproduced light reproduced from the holographic recording medium 4 to the light detector 5. The aperture 62 is placed between the polarization beam splitter 57 and the collecting lens 63, and preferably placed in the imaging plane of sample light, for example, the focal plane of the first relay lens 58 (the position conjugate to the position 33) in order to reduce noises caused by diffracted light of the sample light. FIG. 3(C) is an example of the aperture 62, in which twelve small circular openings 62a arranged in a radial fashion are provided which correspond to the openings 56c in the mask 56 for recording shown in FIG. 3(B).

The collecting lens 63 is provided to collect reproduced light into the light receiving region of the light detector 5, and believed to be available even for a light detector 5 including one light detection element.

The light detector 5 is intended to detect the light intensity of reproduced light reproduced from the holographic recording medium 4. Since the reproduced light is collected by the collecting lens 63 into a small region, a light detector 5 including one light detection element can also be used.

Next, the operation for each processing in the phase object identification device 1 in FIG. 2 will be briefly described. First, in the case of observing a sample and the like, light emitted from the light source 2 is shaped by the beam shaping optical system 51 to provide a required aperture and parallel light, reflected by the pair of mirrors 52 to irradiate the sample and the like, passed through the sample-side objective lens 53 and the imaging lens 54, and reflected by the beam splitter 55 to reach the image sensor 71 for observation. An image of the sample and the like is formed on the light-receiving surface of the image sensor 71 for observation by the sample-side objective lens 53 and the imaging lens 54. Then, the sample positioning means 37 is used to adjust the position of the image and the like so that an image of the sample and the like is arranged in the center in the light-receiving surface of the image sensor 71 for observation, whereas the focusing means 36 is used to make an adjustment so that an image of the sample and the like is brought into focus on the light-receiving surface. With the sample and the like observed as described, the image of the sample and the like is also arranged in the center in the imaging plane 33, and brought into focus, and the reliability in identification and the uniformity in recording can be kept by continuously carrying out the processing for identification and the processing for recording.

In the case of identifying the sample 31 by the phase object identification device 1 in FIG. 2, light emitted from the light source 2 is shaped by the beam shaping optical system 51 to provide a required aperture and parallel light, and reflected by the pair of mirrors 52 to irradiate the sample 31. At least the phase of the light is spatially modulated by the sample 31, and an image of the sample 31 is formed in the position 33 by the sample-side objective lens 53 and the imaging lens 54. The mask 56 in FIG. 3(A) is placed in the position 33, which produces sample light with a circular profile. Then, the sample light is transmitted through the polarization beam splitter 57, formed into an image on the incident pupil plane of the objective lens 61 by the first and second relay lenses 58 and 59, converted by the quarter wavelength plate 60 into circularly polarized light, and subjected to Fourier transformation by the objective lens 61 to irradiate the hologram 41 recorded on the hologram recording layer 43 of the holographic recording medium 4. As a result, the interference between the hologram 41 and the sample light reproduces reproduced light corresponding to reference light for recording if there is a correlation between the hologram 41 and the sample light.

The sample light and reproduced light reflected by the reflective layer is emitted from the holographic recording medium 4, and passed through the objective lens 61, the quarter wavelength plate 60, the second relay lens 59, and the first relay lens 58 in the direction opposite to the direction for irradiation to enter the polarization beam splitter 57. The reproduced light corresponds to reference light for recording, and the reference light is passed through the quarter wavelength plate 60 for conversion into circularly polarized light when the holographic recording medium 4 is irradiated with the reference light. Thus, the light as reproduced light is again passed through the quarter wavelength plate 60 to convert the reproduced light into linearly polarized light in a polarization direction orthogonal to the reference light. Therefore, the reproduced light is reflected by the polarization beam splitter 57 which transmits the reference light, passed through the aperture 62, and collected by the collecting lens 63 into the light detector 5. It is to be noted that the sample light reflected by the reflective layer is emitted from the holographic recording medium 4, passed through the optical systems in the same way as the reproduced light, and reflected by the polarization beam splitter 57, but blocked by the aperture 62.

Furthermore, in order to use multiple holograms 41 for identification, the holographic recording medium 4 is shifted or rotated by the recording medium shifting means 45 while irradiating with sample light in a continuous or pulsed way. Then, the multiple hologram 41 recorded on the holographic recording medium 4 can be irradiated with the sample light in a continuous or intermittent way, and reproduced light can be also detected in a continuous or intermittent way.

The light intensity of the reproduced light varies according to the correlation value (the degree of similarity) between the object light for recording the hologram 41 and the sample light. The larger the value of the light intensity is, the more the object light is similar to the sample light. Therefore, when the object light intensity of the reproduced light exceeds a threshold value determined in advance by experiment or the like, the sample 31 can be identified as a phase object which is coincident with or similar to the known phase object for recording of the hologram 41 reproducing the reproduced light. Alternatively, when reproduced light exceeding the threshold value is not detected, the sample 31 can be identified as a phase object which is not coincident with or similar to the known phase object recorded as the hologram 41 on the holographic recording medium 4. Further, when the intensities of reproduced light from multiple holograms exceed the threshold value, the reproduced light of the highest light intensity is preferably output first as an identification result of similarity.

In the case of recording a known phase object by the phase object identification device 1 in FIG. 2, the sample holding means 3 holds the known phase object. Light emitted from the light source 2 is shaped by the beam shaping optical system 51 to provide a required aperture and parallel light, and reflected by the pair of mirrors 52 to irradiate the known phase object. At least the phase of the light is spatially modulated by the known phase object, and an image of the known phase object is formed in the position 33 by the sample-side objective lens 53 and the imaging lens 54. The mask 56 in FIG. 3(B) is placed in the position 33, which produces object light with a circular profile and twelve small circular rays of reference light arranged around the object light. Then, the object light and reference light is transmitted through the polarization beam splitter 57, formed into an image on the incident pupil plane of the objective lens 61 by the first and second relay lenses 58 and 59, converted by the quarter wavelength plate 60 into circularly polarized light, and subjected to Fourier transformation by the objective lens 61 to irradiate the hologram recording layer 43 of the holographic recording medium 4. As a result, a hologram 41 formed by interference between the object light and the reference light is recorded on the hologram recording layer 43 of the holographic recording medium 4.

Figure 4:
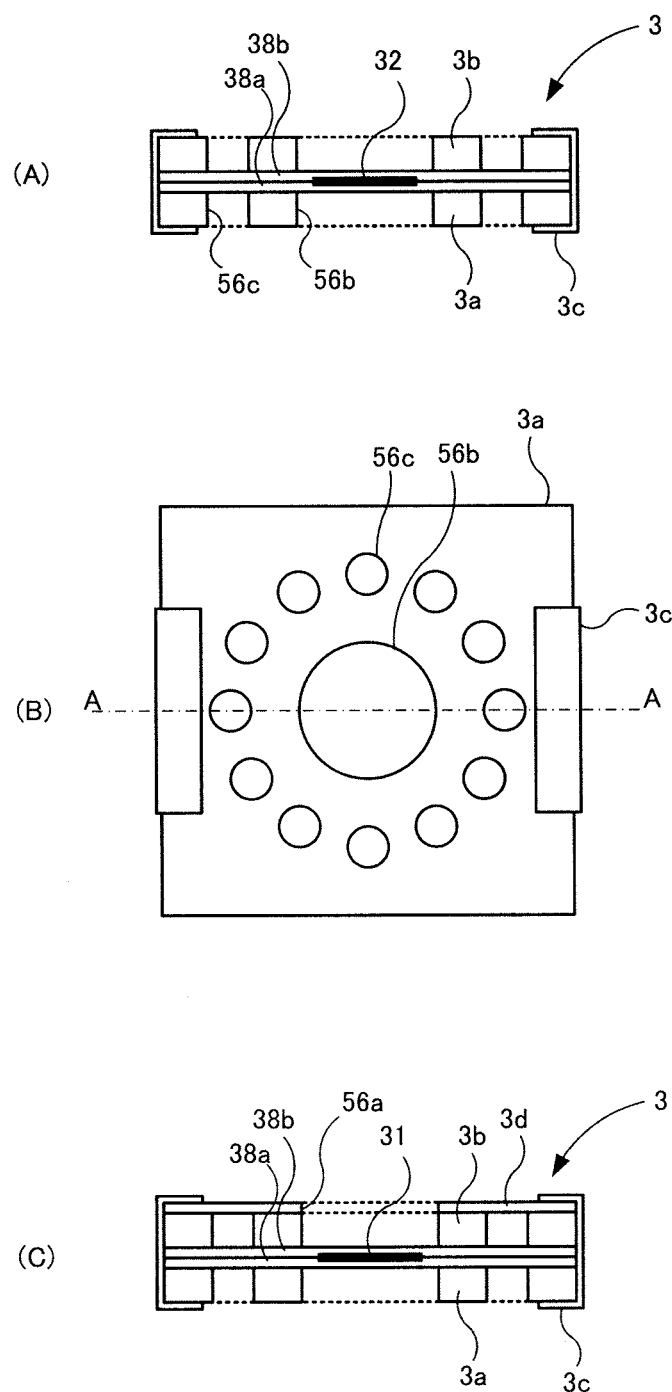
[FIG. 4] (A) a cross-sectional view of a sample holding means for recording; (B) a plan view of FIG. 4(A); and (C) a cross-sectional view of a sample holding means for identification.

FIG. 4 is modification examples of the sample holding means 3, in which the function of the mask 56 is added to the sample holding means 56. FIG. 4(A) is a cross-sectional view of the sample holding means 3 for recording, FIG. 4(B) is a plan view of FIG. 4(A), and FIG. 4(C) is a cross-sectional view of the sample holding means 3 for identification. In FIG. 4(A), the sample holding means 3 includes a pair of light-blocking plate-like members 3a and 3b, slide glass 38a and cover glass 38b with a known phase substance 32 interposed therebetween are arranged between the pair of plate-like members 3a and 3b, and clips 3c clip the pair of plate-like members 3a and 3b to hold the known phase substance 32 via the slide glass 38a and the cover glass 38b. The pair of plate-like members 3a and 3b is provided with openings 56b and 56c as shown in FIG. 4(B). It is to be noted that FIG. 4(A) is a cross section of FIG. 4(B) along the like A-A, and the opening sections are indicated by dotted lines in FIG. 4(A). In the region of the circular opening 56b in the center, the known phase substance 32 is placed which modulates the phase of light from the light source to generate object light. In addition, the openings 56c arranged in a radial fashion around the circular opening 56b generate reference light arranged in a pattern composed of twelve small circular shapes arranged in a radial fashion around the object light. In the configuration of FIG. 4(A), the transparent aids (including colored transparent aids) such as the slide glass 38a and the cover glass 38b enclosing the known phase substance 32 are present in both the opening 56b for generating object light and the openings 56c for generating reference light. Thus, the changes in phase and intensity caused by the aids can be cancelled to record only changes in phase due to the known phase substance 32.

For identification, as shown in FIG. 4(C), a phase object 31 to be identified is enclosed instead of the known phase object 32 between slide glass 38a and cover glass 38b, on which a pair of plate-like members 3a and 3b, and further, a light-blocking member 3d provided with an opening 56a only in the center like the mask 56 in FIG. 3(A) are put, and clipped by clips 3c. The phase object 31 to be identified, which is placed in the region of the opening 56a, can generate sample light with the use of light from the light source, without generating reference light. It is to be noted that the intensity pattern of the reference light is not to be considered limited to the shape and number as in the case of the openings 56c in FIG. 3(B) and FIG. 4(B), as long as at least one opening generates reference light.

Figure 5:
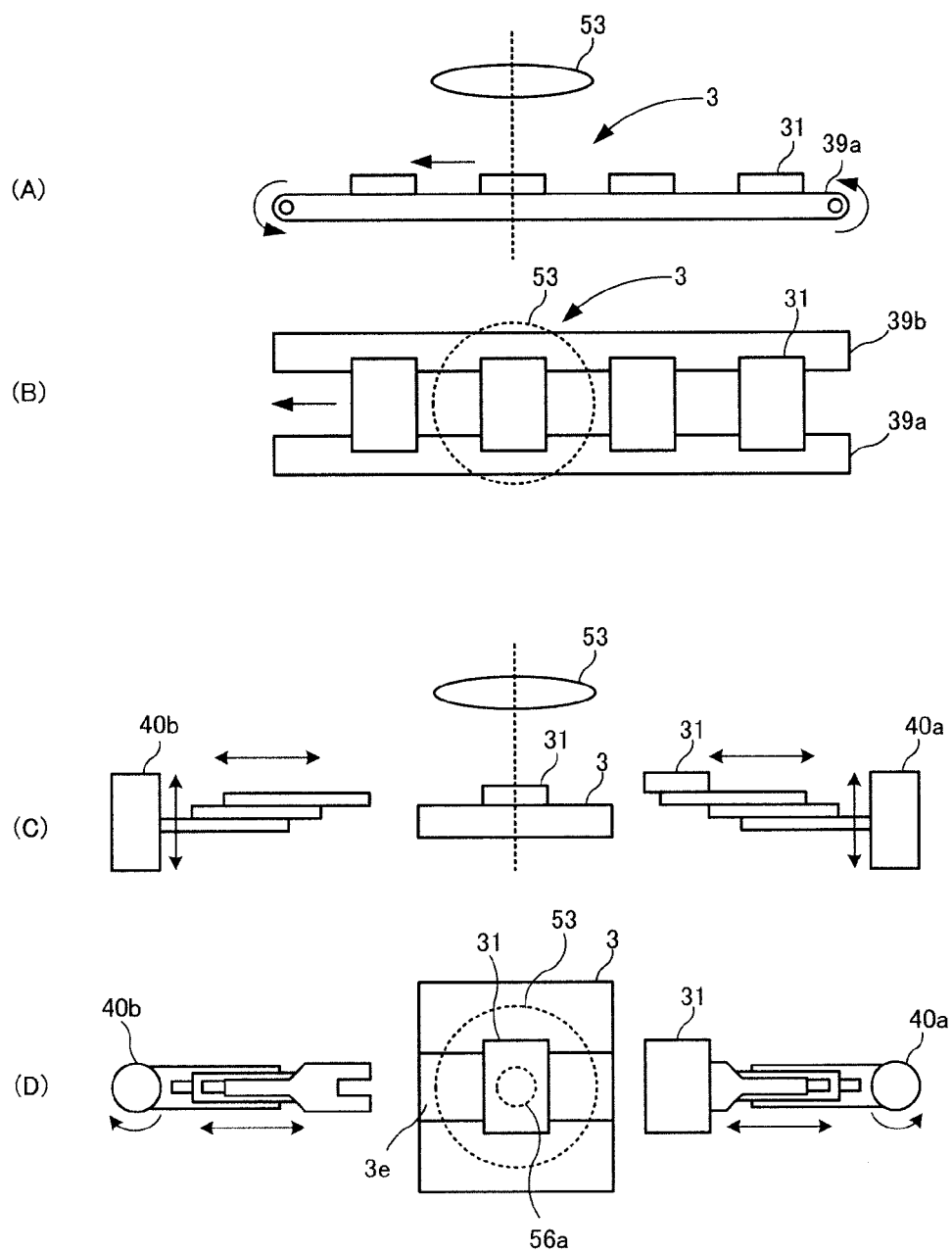
[FIG. 5] (A) to (D) diagrams illustrating examples of sample conveying means.

When the sample holding means 3 is provided with a sample conveying means for sequentially conveying samples 31, the identification of a large number of samples can be carried out continuously. FIG. 5 is an example of the sample conveying means. FIGS. 5(A) and 5(B) are respectively a cross-sectional view and a plan view of belt-conveyer-type sample conveying means 39a and 39b, whereas FIGS. 5(C) and 5(D) are respectively a cross-sectional view and a plan view of conveying-robot-arm-type sample conveying means 40a and 40b. In FIGS. 5(A) and 5(B), the upper and lower edges of samples 31 are held by parallel belt conveyers 39a and 39b, and the samples 31 are sequentially conveyed down the sample-side objective lens 53 by shifting the belt conveyers 39a and 39b. In FIGS. 5(A) and 5(B), the belt conveyers 39a and 39b serve as both the sample holding means 3 and sample conveying means. It is to be noted that, although not shown in the figures, a conveying means for loading the samples 31 onto the belt conveyers 39a and 39b and a conveying means for unloading the samples 31 on the belt conveyers 39a and 39b are respectively provided on the right side and left side of the belt conveyers 39a and 39b in FIG. 5.

In FIGS. 5(C) and 5(D), conveying robot arms 40a and 40b each have a turnable pillar provided with a three-step arm unit in a movable manner in the up-and-down direction and in an extensible manner. The tip of the third arm section from the bottom is configured to be wide so that the samples 31 are placed on the tip. The sample holding means 3 is provided with a concave section 3e in the horizontal direction in the figure, and the tips of the wide arm sections of the conveying robot arms 40a and 40b, on which the samples 31 are placed, should be able to be inserted under the samples 31. The conveying robot arm 40a is intended to convey the samples 31 to the sample holding means 3, whereas the conveying robot arm 40b is intended to carry the samples 31 out of the sample holding means 3. It is to be noted that in FIG. 5(D), a window 56a of a light-transmitting member for transmitting light is provided under the sample 31 on the sample holding means 3 in such a way that the sample 31 is irradiated with light from the light source to enter the sample-side objective lens 53.

Figure 6:
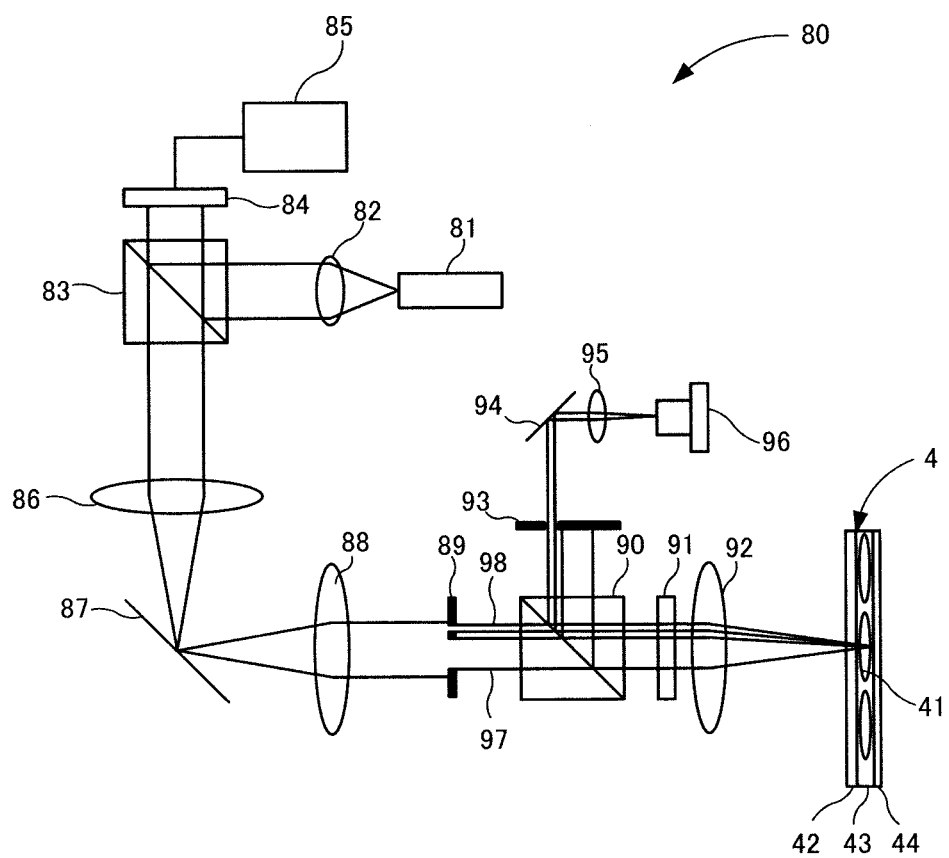
[FIG. 6] a configuration diagram schematically illustrating a recording device which also function as a phase object identification device.

FIG. 6 is an embodiment of a recording device 80 for recording a hologram 41 on a holographic recording medium 4, in which a phase spatial light modulator is adopted as a part of an object light generation means, and the recording device 80 also functions as a phase object identification device with the addition of a configuration for detecting reproduced light. The recording device 80 includes a light source 81, a collimator lens 82, a beam splitter 83, a phase spatial light modulator 84, an information processing device 85, a first relay lens 86, a mirror 87, a second relay lens 88, a mask 89, a polarization beam splitter 90, a quarter wavelength plate 91, an objective lens 92, an aperture 93, a mirror 94, a collecting lens 95, and a light detector 96. FIG. 6 is also a case of a reflection-type holographic recording medium 4.

Light emitted from the light source 81 is shaped into substantially parallel light by the collimator lens 82, and reflected by the beam splitter 83 to enter the phase spatial light modulator 84. The phase spatial light modulator 84 including a plurality of pixels is able to change the phase of incident light for each pixel and spatially modulate the phase of light. FIG. 6 shows a reflection type in which a phase pattern input from the information processing device 85 is displayed on the phase spatial light modulator 84 which reflects incident light while modulating the phase of the incident light in accordance with the displayed phase pattern. As the phase spatial light modulator 84, a parallel-aligned liquid crystal spatial light modulator (PAL-SLM), etc. can be used.

The light reflected by the phase spatial light modulator 84 has a phase modulated in accordance with the phase pattern input from the information processing device 85 as described above. Then, light transmitted through the beam splitter 83 is transmitted by the first and second relay lenses 86 and 88 so that an image of the phase pattern is formed on the incident pupil plane of the objective lens 92. On the way, the light is reflected to change the travelling direction by the mirror 87 arranged in the focal position (Fourier plane) between the first and second relay lenses 86 and 88. The mask 89 is provided to form the profile of object light 97 and the intensity pattern of reference light 98, and preferably arranged on the incident pupil plane of the objective lens 92 and the imaging plane formed by the first and second relay lenses 86 and 88. It is to be noted that if the short focal length of the objective lens 92 makes it physically difficult to arrange the mask 89 on the incident pupil plane in the configuration of FIG. 6, an imaging optical system, not shown, may be further incorporated to arrange the mask 89 in a position conjugate to the incident pupil plane. After that, the light is transmitted through the polarization beam splitter 90, converted by the quarter wavelength plate 91 into circularly polarized light, and subjected to Fourier transformation by the objective lens 92 to irradiate a hologram recording layer 43 of the holographic recording medium 4. As a result, a hologram 41 formed by interference between the object light 97 and the reference light 98 is recorded on the hologram recording layer 43.

In addition, in the recording device 80 in FIG. 6, the phase pattern displayed on the phase spatial light modulator 84 is intended to change the phase of light, which can be said to be a kind of phase object. Then, when any phase pattern is displayed on the phase spatial light modulator 84 as a phase object to be identified, the mask 89 can be changed to carry out processing for identification with the use of the hologram 41 recorded on the holographic recording medium 4. In this case, the phase spatial light modulator 84 serves as a sample holding means.

In the case of allowing the recording device 80 in FIG. 6 to function as a phase object identification device, light emitted from the light source 81 is shaped into substantially parallel light by the collimator lens 82, and reflected by the beam splitter 83 to enter the phase spatial light modulator 84 which reflects the light while modulating the phase of the light in accordance with a phase pattern displayed on the phase spatial light modulator 84. The light reflected by the phase spatial light modulator 84 is transmitted through the beam splitter 83 and transmitted by the first and second relay lenses 86 and 88 so that an image of the phase pattern is formed on the incident pupil plane of the objective lens. On the way, the light is reflected to change the travelling direction by the mirror 87 arranged in the focal position (Fourier plane) between the first and second relay lenses 86 and 88. The mask 89 is provided to form the profile of the sample light, while light is blocked by the opening for shaping the reference light 98 for recording.

After that, the sample light is transmitted through the polarization beam splitter 90, converted by the quarter wavelength plate 91 into circularly polarized light, and subjected to Fourier transformation by the objective lens 92 to irradiate the hologram 41 recorded on a hologram recording layer 43 of the holographic recording medium 4. As a result, the interference between the hologram 41 and the sample light reproduces reproduced light corresponding to the reference light for recording.

The sample light and reproduced light reflected by the reflective layer is emitted from the holographic recording medium 4, and passed through the objective lens 92 and the quarter wavelength plate 91 in the direction opposite to the direction for irradiation to enter the polarization beam splitter 90. The reproduced light corresponds to reference light for recording, and the reference light is passed through the quarter wavelength plate 91 for conversion into circularly polarized light when the holographic recording medium 4 is irradiated with the reference light. Thus, the light as reproduced light is again passed through the quarter wavelength plate 91 to convert the reproduced light into linearly polarized light in a polarization direction orthogonal to the reference light. Therefore, the reproduced light is reflected by the polarization beam splitter 90 which transmits the reference light. In addition, the reflected sample light is also passed through the quarter wavelength plate 91 twice, and thus reflected by the polarization beam splitter 90. The reproduced light is passed through an opening of the aperture 93, whereas the sample light is blocked by the aperture 93. The reproduced light reflected by the mirror 94 is collected by the collecting lens 95 into the light detector 96. It is to be noted that while FIG. 6 shows only one opening for shaping object light and only one opening for shaping reference light as openings of the mask 89 for the sake of convenience, reference light may have multiple intensity patterns.

EXAMPLE 1

The device 80 in FIG. 6 was used to demonstrate the possibility of identifying phase objects. In this example, a Nd:YVO4 laser of 532 nm was used as the light source 81. As the mask 89, masks in the shapes shown in FIGS. 3(A) and 3(B) were used. More specifically, the mask for identification was a mask with a circular opening 56*a* in the center for generating sample light, whereas the mask for recording was a mask with a circular opening 56*b* in the center for generating object light and with twelve small circular openings 56*c* around the circular opening 56*b* in a radial fashion for generating reference light. The openings 56*a* and 56*b* for the profile of sample light or object light had a circular shape with a diameter of 1 mm, whereas the openings 56*c* for generating reference light had a circular shape with a diameter of 0.29 mm. In addition, the objective lens 92 had NA of 0.55 and a focal length of 4 mm.

Figure 7:
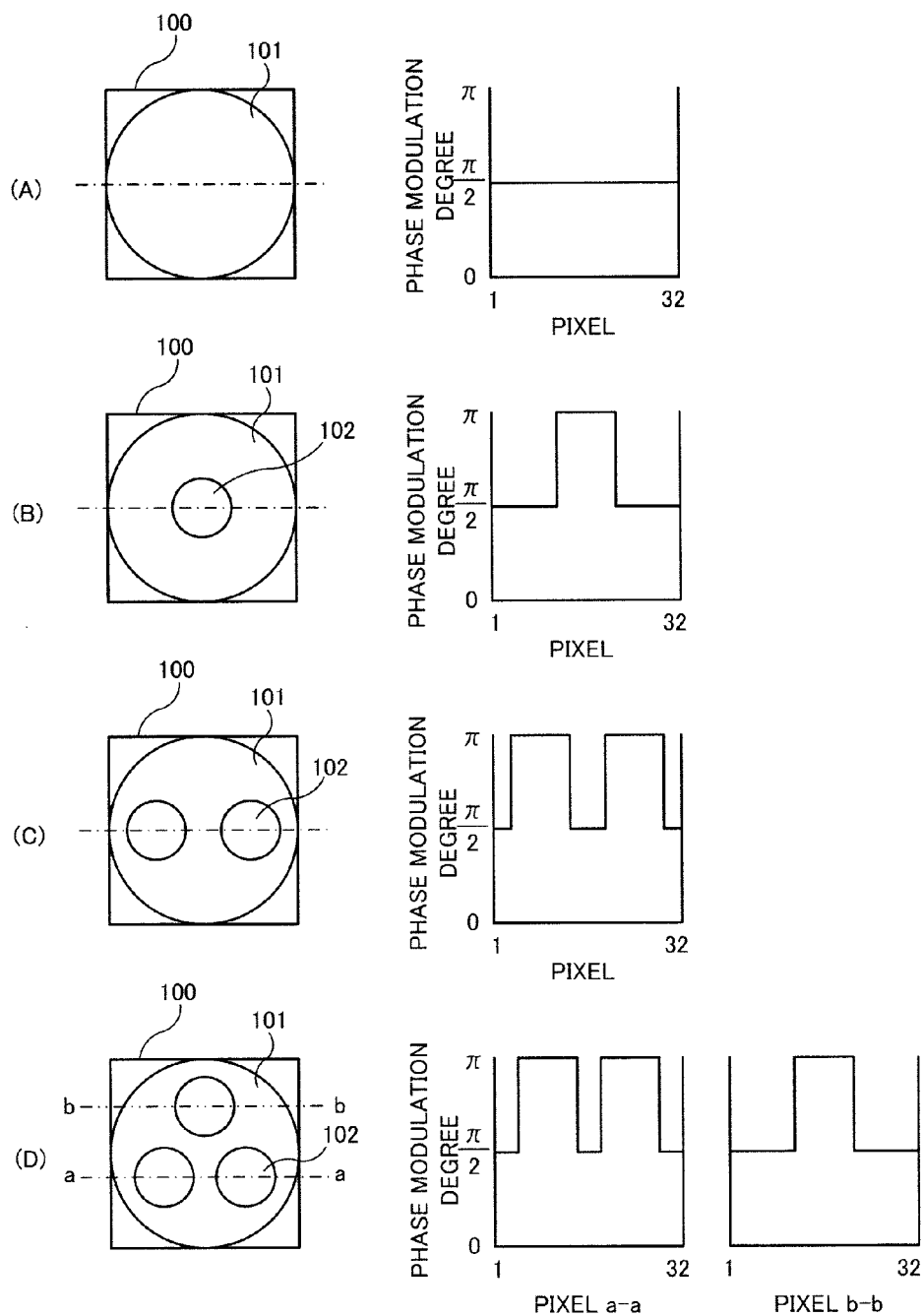
[FIG. 7] diagrams illustrating phase patterns in a display region of a phase spatial light modulator.

First, four types of holograms 41 were recorded on the holographic recording medium 4. Phase patterns in FIGS. 7(A) to 7(D) were displayed on a display region of 32×32 pixels of the phase spatial light modulator 84 to generate object light for each phase pattern, and record holograms by interference between the object light and the reference light. FIGS. 7(A) to 7(D) show phase patterns on the display surface on the left side, and show the phase modulation degrees in cross sections along an alternate long and short dash line or an alternate long and two short dashes line on the right side. FIG. 7(A) displays a circular pattern 101 with a phase modulation degree of $\pi/2$ and a diameter of 32 pixels in a display region 100. FIG. 7(B) displays a circular pattern 101 with a phase modulation degree of $\pi/2$ and a diameter of 32 pixels in a display region 100 and displays a circular pattern 102 with a phase modulation degree of $\pi$ and a diameter of 10 pixels in the center of the circular pattern 101. FIG. 7(C) displays a circular pattern 101 with a phase modulation degree of $\pi/2$ and a diameter of 32 pixels in a display region 100 and displays two circular patterns 102 with a phase modulation degree of $\pi$ and a diameter of 10 pixels in the center of the circular pattern 101. FIG. 7(D) displays a circular pattern 101 with a phase modulation degree of $\pi/2$ and a diameter of 32 pixels in a display region 100 and displays three circular patterns 102 with a phase modulation degree of $\pi$ and a diameter of 10 pixels in the center of the circular pattern 101. It is to be noted that FIG. 7(D) shows the phase modulation degrees in a cross section along the line a-a and a cross section along the line b-b on the right side. Hereinafter, the holograms in accordance with the phase patterns in FIGS. 7(A) to 7(D) are respectively referred to as holograms A to D.

Figure 8:
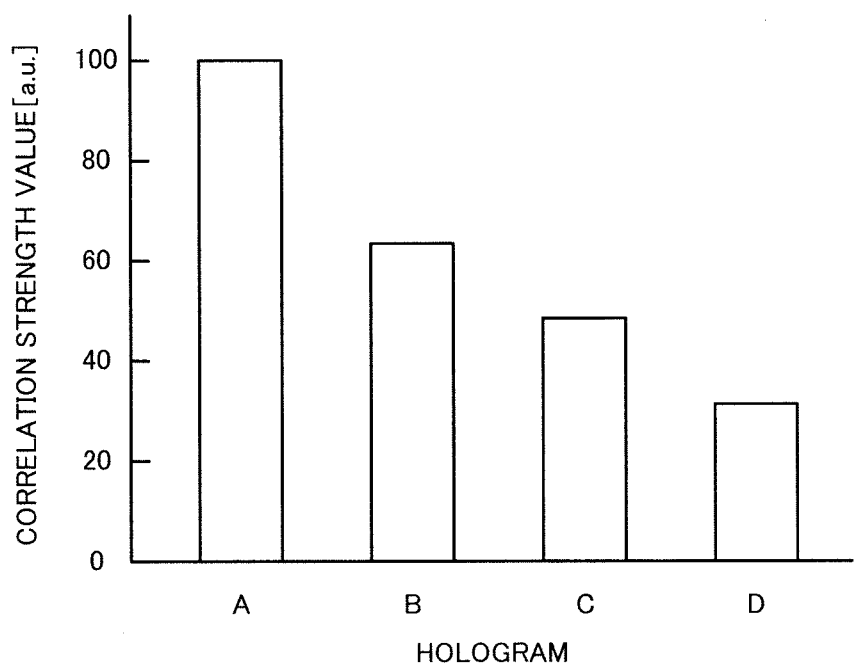
[FIG. 8] a diagram showing the results of detecting reproduced light reproduced from holograms A to D.

Next, in accordance with the phase pattern of the circular pattern 101 with a phase modulation degree of $\pi/2$ and a diameter of 32 pixels, which is displayed in the display region 100 in FIG. 7(A), the phase of light was modulated to generate sample light, and the holograms A to D were each irradiated with the sample light. FIG. 8 shows the results of detecting reproduced light reproduced from the holograms A to D, where the vertical axis indicates a correlation value (the intensity of reproduced light) in terms of arbitrary unit, normalized by a correlation value of autocorrelation, and the horizontal axis indicates the respective holograms A to D. The hologram A recorded with the use of the object light in accordance with the phase pattern in FIG. 7(A) is coincident with the sample light, and thus has autocorrelation. The hologram B recorded in accordance with the phase pattern with the circular pattern 102 displayed with a phase modulation degree of $\pi$ and a diameter of 10 pixels in FIG. 7(B), has cross-correlation with the phase pattern in FIG. 7(A) corresponding to the sample light, but has a higher correlation value of 63 as compared with the holograms C and D because of a small difference in phase pattern. The holograms C and D each have correlation values 48 and 31, and it can be thus confirmed that the correlation value is decreased with increase in the difference (the number of circular patterns 102 with a phase modulation degree of $\pi$ and a diameter of 10 pixels) with respect to the phase pattern in FIG. 7(A) corresponding to the sample light. This suggests that it is possible to identify the number of cells, the presence or absence of a cell nucleus, etc. in the phase object identification device according to the present invention.

EXAMPLE 2

The device 80 in FIG. 6 was used to demonstrate the possibility of identifying phase objects in response to change in phase. The device in this example had the same conditions as in Example 1. First, the phase was changed by $\pi/4$ from 0 to $2\pi$ for all of the pixels in the display region of 32×32 pixels of the phase spatial light modulator 84 to generate object light for each pixel, and record nine holograms by interference between the object light and the reference light. More specifically, the object light in accordance with the phase patterns in which the phase was set to 0, $\pi/4$, $\pi/2$, $\pi/4$, $\pi$, $5\pi/4$, $3\pi/2$, $7\pi/4$, and $2\pi$ for all of the pixels in the display region was used to record holograms 0, $\pi/4$, $\pi/2$, $3\pi/4$, $\pi$, $5\pi/4$, $3\pi/2$, $7\pi/4$, and $2\pi$.

These nine holograms were irradiated with sample light generated in accordance with a phase pattern in which the phase was set to 0 for all of the pixels in the display region.

Figure 9:
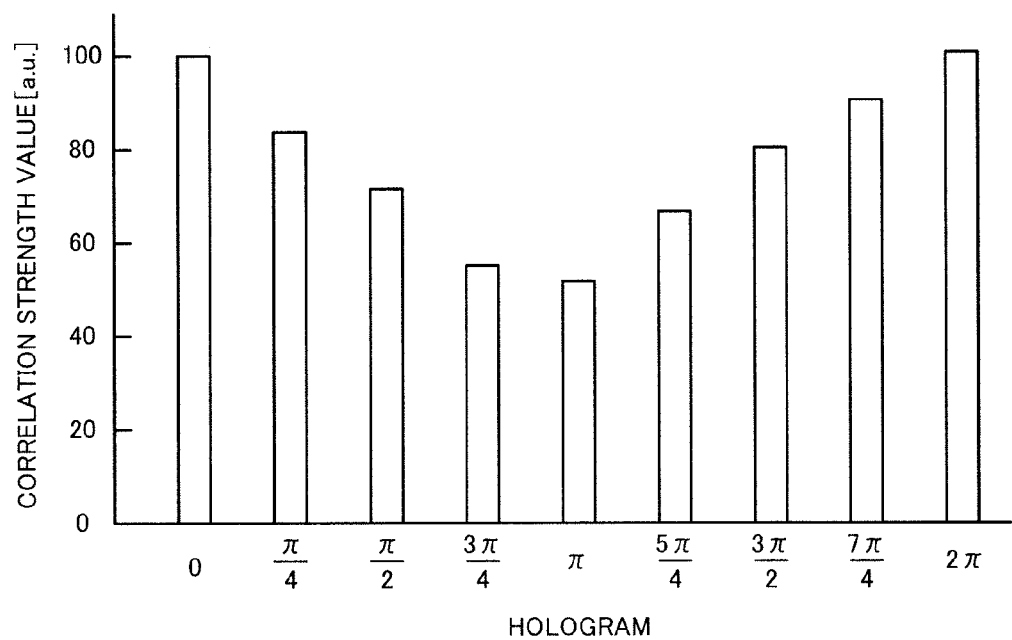
[FIG. 9] a diagram showing the results of detecting reproduced light reproduced from holograms 0 to $2\pi$.

FIG. 9 shows the results of detecting reproduced light reproduced from the holograms 0, π/4, π/2, 3π/4, π, 5π/4, 3π/2, 7π/4, and 2π, where the vertical axis indicates a correlation value (the intensity of reproduced light) in terms of arbitrary unit, normalized by a correlation value of autocorrelation, and the horizontal axis indicates the respective holograms. The hologram 0 and the hologram 2π recorded with the use of the object light in accordance with the phase patterns with the phase of 0 for all of the pixels is coincident with the sample light, and thus has autocorrelation. The correlation value is larger when the hologram of interest is closer to the hologram 0 and the hologram 2π, and smaller when the hologram of interest is further from the hologram 0 and the hologram 2π, and the hologram π has the smallest correlation value. According to Example 2, the phase difference between the phase object to be identified and the known phase object can be identified as the intensity of the reproduced light. Furthermore, it is suggested that the application of Example 2 allows vibrations of cells, expansions of cells, and dynamic changes in phase to be observed or identified.

DESCRIPTION OF THE REFERENCE NUMERALS 1 phase object identification device
2 light source
3 sample holding means
4 holographic recording medium
5 light detector
6 recording device
21 light emitted from a light source
22 sample light
23 reproduced light
24 object light
25 reference light
31 phase object to be identified (sample)
32 known phase object
41 hologram
42 substrate
43 hologram recording layer
44 substrate

The invention claimed is:

1. A phase object identification device for detecting a correlation between a phase object to be identified and a known phase object, the device comprising:
    a light source;
    sample holding means for holding a phase object to be identified comprising sample positioning means for shifting the phase object to be identified in a planar direction orthogonal to an optical axis;
    an observation optical system comprising a sample-side objective lens and an imaging lens or an eyepiece for observing an image of the phase object to be identified, the phase object held by the sample holding means, the observation optical system configured to form the image of the phase object to be identified;
    focusing means for changing the distance between the phase object to be identified and the sample-side objective lens;
    a holographic recording medium on which a hologram formed by interference between reference light and object light that is phase-modulated by a phase pattern of a known phase object is recorded;
    a light detector; and
    an identification optical system in which a phase of light emitted from the light source is modulated by a phase pattern of the phase object to be identified to generate sample light, the hologram of the holographic recording medium is irradiated with the sample light, and reproduced light reproduced from the hologram of the holographic recording medium is detected by the light detector, and
    the sample-side objective lens of the observation optical system is also used as an optical component of the identification optical system,
    wherein the observation optical system comprises a beam splitter configured to direct a portion of the generated sample light to an image sensor, and wherein the image of the phase object to be identified is formed by the image sensor utilizing said portion of the generated sample light that is excluded from passing through the hologram of the holographic recording medium.

2. The phase object identification device according to claim 1, characterized in that the hologram of the holographic recording medium is irradiated with the sample light by an objective lens arranged in such a way that a real image of the phase object to be identified is located on an incident pupil plane.

3. The phase object identification device according to claim 1, characterized in that multiple holograms formed from multiple known phase objects are recorded on the holographic recording medium, and
    the phase object identification device comprises irradiated position shifting means for shifting a position irradiated with the sample light in the holographic recording medium.

4. The phase object identification device according to claim 1, characterized in that it comprises sample conveying means for sequentially conveying multiple phase objects to be identified to the sample holding means.

5. The phase object identification device according to claim 1, characterized in that the phase object to be identified is a biological cell or a bacterium, and the presence or absence of a cell nucleus in the biological cell or the bacterium is identified.

6. The phase object identification device according to claim 1, characterized in that the known phase object is a specimen within standards, and whether or not the phase object to be identified corresponds to the standards is identified.

7. The phase object identification device according to claim 1, characterized in that it comprises reference light generation means for generating reference light,
    the sample holding means is able to hold a known phase object, a phase of light emitted from the light source is modulated by a phase pattern of the known phase object to generate object light, the reference light generation means generates reference light, the holographic recording medium is irradiated with the object light and the reference light, and a hologram formed by interference between the object light and the reference light is recorded on the holographic recording medium.

8. The phase object identification device according to claim 7, characterized in that the reference light generation means is an opening formed in the sample holding means.

9. A phase object identification method comprising the steps of:
    observing an image of a phase object to be identified utilizing an observation optical system;
    adjusting a size of the observed image of the phase object to be identified by changing a distance between a sample-side objective lens of the observation optical system and the phase object to be identified;

adjusting a position of the observed image of the phase object to be identified by shifting the phase object to be identified in a planar direction orthogonal to an optical axis of the observation optical system, wherein, with the size and the position of the observed image of the phase object to be identified adjusted, a phase of light emitted from a light source is modulated by the phase pattern of the phase object to be identified to generate sample light;

irradiating with the generated sample light a holographic recording medium, on which a hologram formed by interference between reference light and object light that is phase-modulated by a phase pattern of a known phase object is recorded; and detecting reproduced light reproduced from the hologram of the holographic recording medium by a light detector;

wherein the observation optical system comprises a beam splitter configured to direct a portion of the generated sample light to an image sensor, and wherein the image of the phase object to be identified is formed by the image sensor utilizing the portion of the generated sample light that is excluded from passing through the hologram of the holographic recording medium; and wherein the phase object to be identified is identified as having a correlation with the known phase object if the intensity of the reproduced light detected by the light detector is greater than a threshold value, or the phase object to be identified is identified as having no correlation with the known phase object if the intensity of the reproduced light is less than the threshold value.

* * * * *